US00PP16984P2

(12) United States Plant Patent
Verwer

(10) Patent No.: US PP16,984 P2
(45) Date of Patent: Aug. 15, 2006

(54) ***DAHLIA* PLANT NAMED 'HS FIRST LOVE'**

(50) Latin Name: *Dahlia hybrida*
Varietal Denomination: 'HS First Love'

(75) Inventor: Aad W. M. Verwer, Lisse (NL)

(73) Assignee: Verwer Dahlia'B.V., Lisse (NL)

( * ) Notice: Subject to any disclaimer, the term of this patent is extended or adjusted under 35 U.S.C. 154(b) by 26 days.

(21) Appl. No.: 11/146,221

(22) Filed: Jun. 6, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'HS First Love', characterized by its upright and outwardly spreading plant habit; freely branching growth habit; dark-colored foliage; early and freely flowering habit; daisy inflorescence form; large inflorescences with salmon pink and red bi-colored ray florets; and good postproduction longevity and garden performance.

1 Drawing Sheet

Botanical designation: *Dahlia hybrida.*
Cultivar denomination: 'HS First Love'.

CROSS-REFERENCE TO RELATED APPLICATIONS

Dahlia Plant Named 'HS Romeo'; Aad W. M. Verwer, Applicant; disclosed in U.S. Plant Patent application Ser. No. 11/146,232.

BACKGROUND OF THE INVENTION

The present Invention relates to a new and distinct cultivar of *Dahlia* plant, botanically known as *Dahlia hybrida* and hereinafter referred to by the name 'HS First Love'.

The new *Dahlia* is a product of a planned breeding program conducted by the Inventor in Lisse, The Netherlands. The objective of the breeding program is to create new compact potted *Dahlia* cultivars that have a freely branching growth habit, dark green-colored foliage, early and freely flowering habit, daisy inflorescence form, attractive ray floret coloration, inflorescences that are not persistent, and good postproduction longevity and garden performance.

The new *Dahlia* originated from a chance open-pollination in 2000 of a proprietary selection of *Dahlia hybrida* identified as code number Vd1-216, not patented, as the female, or seed, parent with an unknown selection of *Dahlia hybrida* as the male, or pollen, parent. The new *Dahlia* was discovered and selected by the Inventor as a single flowering plant within the progeny of the stated open-pollination grown in a controlled environment in Lisse, The Netherlands in 2001.

Asexual reproduction of the new *Dahlia* by cuttings was first conducted in Lisse, The Netherlands during the spring of 2002. Asexual reproduction by cuttings has shown that the unique features of this new *Dahlia* are stable and reproduced true to type in successive generations.

SUMMARY OF THE INVENTION

The cultivar HS First Love has not been observed under all possible environmental conditions. The phenotype may vary somewhat with variations in environment such as temperature and light intensity without, however, any variance in genotype.

The following traits have been repeatedly observed and are determined to be the unique characteristics of 'HS First Love'. These characteristics in combination distinguish 'HS First Love' as a new and distinct *Dahlia* cultivar:

1. Upright and outwardly spreading plant habit.
2. Freely branching growth habit.
3. Dark-colored foliage.
4. Early and freely flowering habit.
5. Daisy inflorescence form.
6. Large inflorescences with salmon pink and red bi-colored ray florets.
7. Good postproduction longevity and garden performance.

Plants of the new *Dahlia* differ primarily from plants of the female parent selection in the following characteristics:

1. Plants of the new *Dahlia* are more compact than plants of the female parent selection.
2. Plants of the new *Dahlia* and the female parent selection differ in ray floret coloration.

Plants of the new *Dahlia* can be compared to the *Dahlia* cultivar HS Romeo, disclosed in U.S. Plant patent application Ser. No. 11/146,232. Plants of the new *Dahlia* differ from plants of the cultivar HS Romeo primarily in ray floret coloration.

Plants of the new *Dahlia* can also be compared to plants of the cultivar Sunshine, not patented. In side-by-side comparisons conducted in Lisse, The Netherlands, plants of the new *Dahlia* differed from plants of the cultivar Sunshine in the following characteristics:

1. Plants of the new *Dahlia* were smaller than plants of the cultivar Sunshine.
2. Plants of the new *Dahlia* were more freely branching than plants of the cultivar Sunshine.
3. Plants of the new *Dahlia* had darker-colored leaves than plants of the cultivar Sunshine.

4. Plants of the new *Dahlia* were more freely flowering than plants of the cultivar Sunshine.
5. Plants of the new *Dahlia* had smaller inflorescences than plants of the cultivar Sunshine.
6. Ray florets of plants of the new *Dahlia* were salmon pink and red bi-colored ray florets of plants of the cultivar Sunshine were yellow orange in color.
7. Plants of the new *Dahlia* had more and larger disc florets per inflorescence than plants of the cultivar Sunshine.
8. Plants of the *Dahlia* had longer peduncles than plants of the cultivar Sunshine.

BRIEF DESCRIPTION OF THE PHOTOGRAPH

The accompanying colored photograph illustrates the overall appearance of the new *Dahlia* showing the colors as true as it is reasonably possible to obtain in colored reproductions of this type. Colors in the photograph may differ from the color values cited in the detailed botanical description which accurately describe the colors of the new *Dahlia*. The photograph comprises a side perspective view of a typical flowering plant of 'HS First Love'.

DETAILED BOTANICAL DESCRIPTION

In the following description, color references are made to The Royal Horticultural Society Colour Chart, 1995 Edition, except where general terms of ordinary dictionary significance are used. The aforementioned photograph and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three to four weeks after planting rooted cuttings. Plants were about four months old when the photographs and the description were taken.

Botanical classification: *Dahlia hybrida* cultivar HS First Love.

Parentage:

*Female, or seed, parent.*—Proprietary selection of *Dahlia hybrida* identified as code number Vd1-216, not patented.

*Male, or pollen, parent.*—Unknown selection of *Dahlia hybrida,* not patented.

Propagation:

*Type.*—By vegetative cuttings.

*Time to initiate roots.*—Summer: About three days at 17° C. Winter: About four days at 17° C.

*Time to produce a rooted young plant.*—Summer: About 12 days at 17° C. Winter: About 15 days at 17° C.

*Root description.*—Fine, fibrous; older roots, fleshy.

*Rooting habit.*—Freely branching; dense.

*Tuber description.*—Tuber development has not been observed.

Plant description:

*Appearance.*—Perennial daisy-type potted *Dahlia.* Upright and outwardly spreading plant habit; inverted triangle. Freely branching habit, about four lateral branches; dense and full plants. Vigorous growth habit.

*Plant height.*—About 50 cm.

*Plant diameter.*—About 40 cm.

*Lateral branch description.*—Length: About 30 to 45 cm. Diameter: About 3 mm. Internode length: About 15 to 20 cm. Strength: Strong. Texture: Glabrous, smooth. Color: 187B.

*Foliage description.*—Arrangement: Leaves opposite; leaves may be single or compound with three or five leaflets. Shape: Ovate. Apex: Acuminate. Base: Attenuate. Margin: Serrate; sinuses divergent. Length: Single leaves: About 7 cm. Compound leaves with three leaflets: About 12 cm. Compound leaves with five leaflets: About 17 cm. Width: Single leaves: About 4 cm. Compound leaves with three leaflets: About 10 cm. Compound leaves with five leaflets: About 14 cm. Venation pattern: Pinnate. Texture, upper and lower surfaces: Smooth, glabrous. Color: Developing foliage, upper surface: Between 200A and 187B. Developing foliage, lower surface: Darker than 198A. Fully expanded foliage, upper surface: More purple than 200A. Fully expanded foliage, lower surface: Darker than 200A. Venation, upper surface: 59A. Venation, lower surface: 59B. Petiole length: Single leaves: About 8 mm. Compound leaves with three leaflets: About 3 mm. Compound leaves with five leaflets: About 4 cm. Petiole diameter: Single leaves: About 3 mm. Compound leaves with three leaflets: About 3 mm. Compound leaves with five leaflets: About 3 mm. Petiole color, upper surface: 59A. Petiole color, lower surface: 59B.

Inflorescence description:

*Appearance.*—Daisy inflorescence form; inflorescences rotate. Inflorescences borne on terminals, arising from leaf axils, positioned above the foliage. Ray and disc florets develop acropetally on the receptacle. Inflorescences not fragrant. Inflorescences persistent.

*Flowering response.*—Flowering recurrent to continuous during the summer and autumn in The Netherlands. Early flowering habit, plants start flowering about 60 days after planting.

*Postproduction longevity.*—On the plant, inflorescences maintain good color and substance for about ten to twelve days in an outdoor environment. As cut flowers, inflorescences maintain good color and substance for about five days in an indoor environment.

*Quantity of inflorescences per flowering stem.*—About 70 inflorescences and inflorescence buds per plant.

*Inflorescence size.*—Diameter: About 8 cm. Depth (height): About 1.5 cm. Diameter of disc: About 2.5 cm. Receptacle diameter: About 1.8 cm. Receptacle height: About 5 mm.

*Inflorescence buds.*—Length: About 1 cm. Diameter: About 1.9 cm. Shape: Oblate. Color: Towards the apex, 166B; towards the base, 200A.

*Ray florets.*—Number of ray florets per inflorescence: About eight in a single whorl. Length, fully developed: About 3.2 cm. Width, fully developed: About 2.1 cm. Orientation: Initially upright, eventually close to perpendicular to the peduncle; mostly flat. Shape: Ovate. Apex: Obtuse or emarginate. Base: Attenuate. Margin: Entire. Texture, upper and lower surfaces: Smooth, glabrous; velvety. Venation pattern: Parallel. Color: When opening and fully opened, upper surface: 29A; towards the base, 22A; at the base, 46B; color becomes closer to 29D with development. When opening and fully opened, lower surface: 16A blushed with 22B especially along the veins.

*Disc florets.*—Number of disc florets per inflorescence: About 120. Length: About 1.1 cm. Width, at the apex: About 1.5 mm. Width, at the base: About 1 mm. Shape: Tubular, elongated. Apex: Pentafid. Base: Attenuate. Color: Immature: 179A. Mature: Apex: 179A. Mid-section: 179A. Base: 154D.

*Phyllaries.*—Quantity/arrangement: One whorl with about five phyllaries per inflorescence. Length: About 8 mm. Width: About 4 mm. Shape: Ovate. Apex: Acute. Base: Attenuate. Margin: Entire. Texture, upper and lower surfaces: Smooth, glabrous; leathery. Color, upper surface: Darker than 200A. Color, lower surface: 200A.

*Peduncles.*—Length, terminal peduncles: About 50 cm. Length, fourth peduncle: About 20 cm. Diameter: Towards the base, about 9 mm; towards the apex, about 2 mm. Angle: Erect to about 20° from vertical. Strength: Strong. Texture: Glabrous, smooth. Color: 183A.

*Reproductive organs.*—Androecium: Present on disc florets only. Stamen quantity: About five per floret. Anther shape: Linear. Anther length: About 6 mm. Anther color: 16A. Pollen amount: Abundant. Pollen color: 21A. Gynoecium: Present on ray and disc florets. Pistil quantity: One per floret. Pistil length: About 4 mm. Stigma shape: Lanceolate. Stigma color: 12B. Style length: About 4 mm. Style color: 150B. Ovary color: 8A.

*Seeds.*—Length: About 6 mm. Diameter: About 1.1 mm. Color: Darker than 199B.

Disease/pest resistance: Resistance to pathogens and pests common to *Dahlias* has not been observed on plants grown under commercial greenhouse or outdoor conditions.

Weather tolerance: Plants of the new *Dahlia* have been observed to be very tolerant to wind, rain and full sun conditions. Plants of the new *Dahlia* have been observed to tolerate temperatures from 0 to 40° C.

It is claimed:

1. A new and distinct cultivar of *Dahlia* plant named 'HS First Love', as illustrated and described.

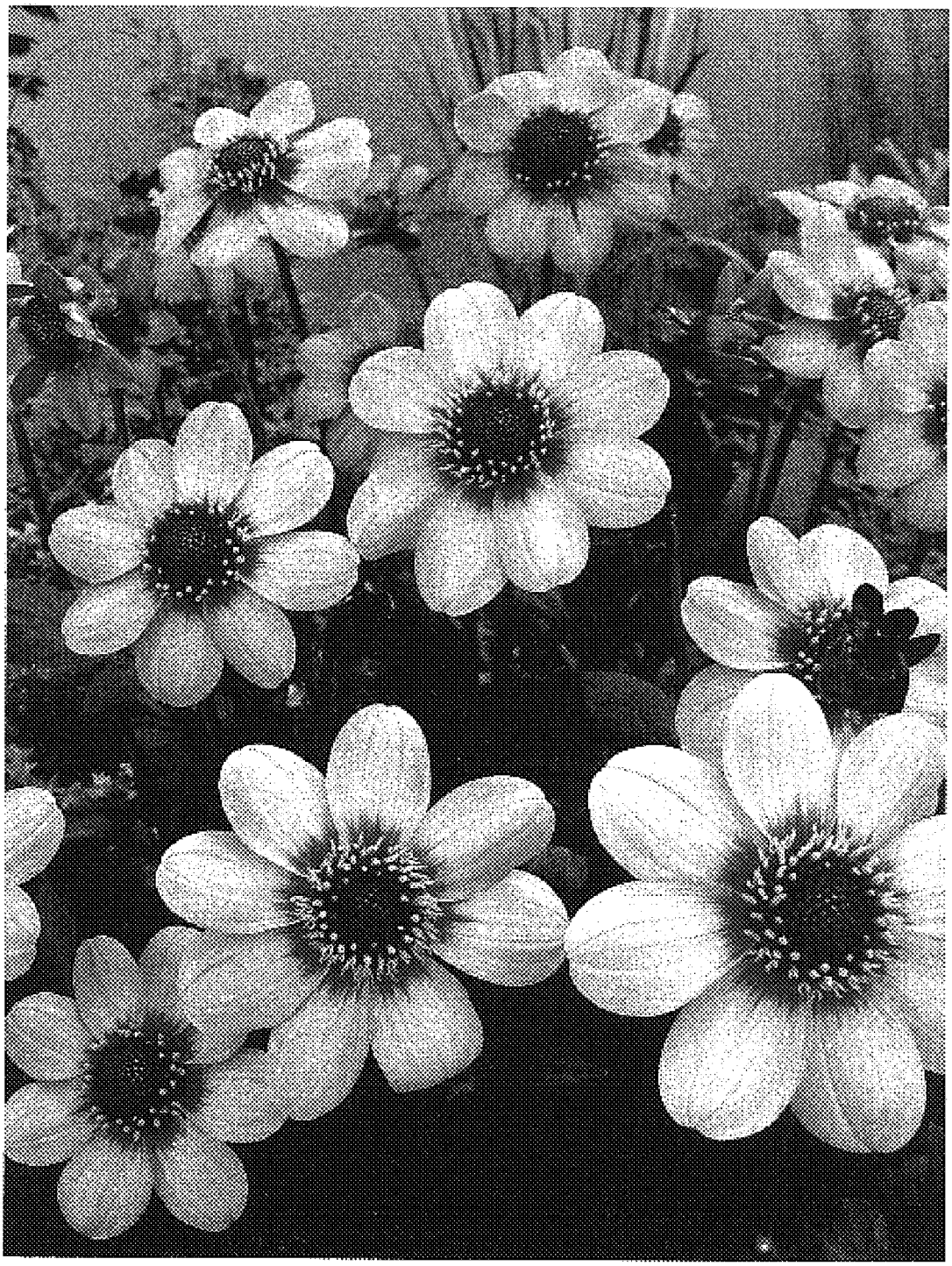

* * * * *